United States Patent [19]
Britton et al.

[11] Patent Number: 5,585,642
[45] Date of Patent: Dec. 17, 1996

[54] BEAMLINE CONTROL AND SECURITY SYSTEM FOR A RADIATION TREATMENT FACILITY

[75] Inventors: Barrie G. Britton, Riverside; David A. Lesyna; Jon W. Slater, both of Redlands, all of Calif.

[73] Assignee: Loma Linda University Medical Center, Loma Linda, Calif.

[21] Appl. No.: 388,953

[22] Filed: Feb. 15, 1995

[51] Int. Cl.⁶ ..................................... G21G 1/10
[52] U.S. Cl. ........................... 250/492.3; 250/398
[58] Field of Search ................. 250/492.1, 457.3, 250/398; 378/65

[56]        References Cited

U.S. PATENT DOCUMENTS

| 3,783,251 | 1/1974 | Paukovich | 364/413.36 |
| 4,870,287 | 9/1989 | Cole | 250/492.3 |
| 5,190,516 | 3/1993 | Bronn | 600/1 |
| 5,260,581 | 11/1993 | Lesyna et al. | |
| 5,317,164 | 5/1994 | Kurokawa | 250/492.3 |

FOREIGN PATENT DOCUMENTS

| 0586152 | 3/1994 | European Pat. Off. | |
| 8805321 | 7/1988 | WIPO | |
| 9429882 | 12/1994 | WIPO | |
| 9501207 | 1/1995 | WIPO | |

*Primary Examiner*—Bruce C. Anderson
*Attorney, Agent, or Firm*—Knobbe, Martens, Olson & Bear

[57]        ABSTRACT

The present invention is directed to a method and apparatus for beamline security in radiation beam treatment facilities. The system monitors and controls the radiation beam steering system to safeguard against wrong-path and multiple-path conditions which could otherwise lead to accidental radiation exposure. One aspect of the method involves comparing the beam path configuration signals to signals corresponding to a requested beam configuration to check for agreement, as well as singular path configuration. Controller checks are performed using complimentary-redundant logical communication paths applied to the state of the beam steering system. Upon detection of any one of several possible error conditions, such as over-heating, communication link failure, unauthorized personnel entry and multiple path condition, the beamline power supplies are disabled, preventing transfer of the radiation beam to the treatment room.

28 Claims, 11 Drawing Sheets

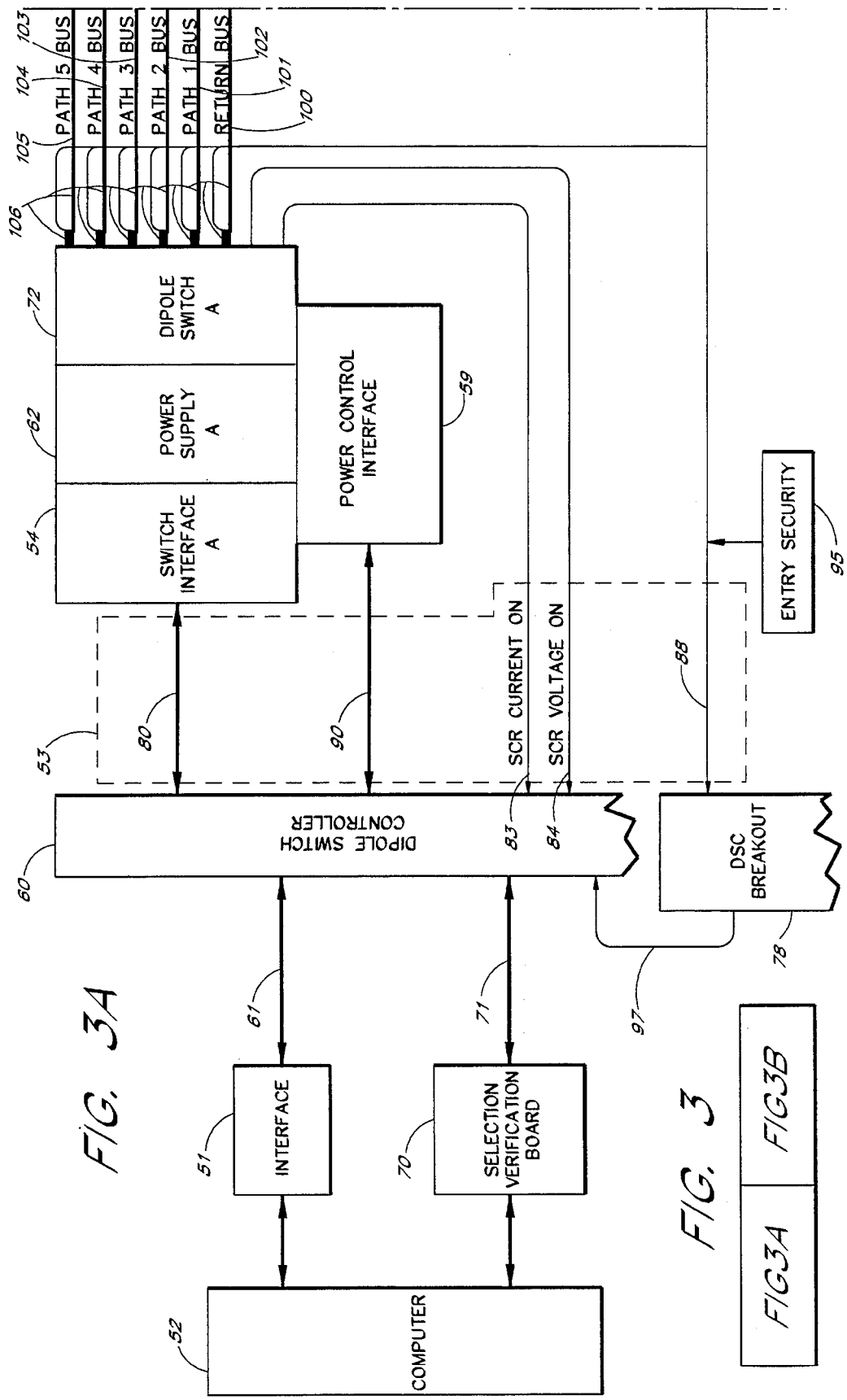

BEAMLINE CONTROL AND SECURITY SYSTEM FOR A RADIATION TREATMENT FACILITY

FIELD OF THE INVENTION

The present invention generally relates to control and security systems for radiation treatment facilities. In particular, the invention pertains to beamline control and security systems for proton therapy facilities and to systems for controlling, detecting and preventing hazardous conditions to patients, personnel and facility apparatus.

BACKGROUND OF THE INVENTION

Contemporary radiation therapy utilizes several types of ionizing radiation, such as β-rays, γ-rays, X-rays and high-energy protons applied to malignant tissue to prevent and control the spread of cancer. Proton beam therapy, in particular, has undergone dramatic development in recent years with attendant advances in therapy techniques and facilities. In most proton therapy systems around the world, the proton accelerators were originally built for physics research and later adapted for part-time clinical research and therapy. However, the imminent advantages of proton beam therapy is best realized with the development of dedicated, clinically based facilities. One such therapy facility, located at the Loma Linda University Medical Center, was purposely built to provide therapeutic proton beams to a multiplicity of treatment rooms, thereby increasing patient throughput and defraying the cost of an otherwise expensive form of treatment. An overview of the facility and its development is provided in "The Proton Treatment Center at Loma Linda University Medical Center: Rationale for and Description of its Development," J. M. Slater, et al., *Intl. J. Radiation Oncology*, vol. 22, no. 2, 1992, pp.383–389, and herein incorporated by reference. A more detailed description of the proton beam apparatus and facility is provided in U.S. Pat. No. 4,870,287 by F. T. Cole, et al., entitled "Multi-Station Proton Beam Therapy System," also herein incorporated by reference.

Proton radiation beamlines operate using large high-field electromagnets for beam deflection and focussing. At the Loma Linda Facility, the proton beam is generated with an on-site proton synchrotron and transferred by such beamlines to any one of several target destinations. To insure protection from proton radiation exposure, the beamline magnets must be monitored and controlled to prevent beam misdirection and mistiming. To this end, a method of treatment room selection verification has been employed by which a selected or desired beam path implementation is verified before authorizing beam delivery. The method of selection verification is more fully disclosed in U.S. Pat. No. 5,260,581, herein incorporated by reference. While such a method appears to be a necessary safeguard from radiation misexposure, it does not detect all potentially hazardous fault conditions. The collection of such magnets often require megawatts of electrical power, which itself presents a lethal hazard to facility personnel if appropriate safeguards are not taken to insure personnel non-contact. Thus, in addition to properly coordinating and timing the magnet array, appropriate measures should be taken to insure against mechanical, electrical and thermal breakdown. In the event of component failure, by any means, the high-power apparatus should be disabled and the radiation beam directed to a so-called "beam dump." Clearly, meeting these challenging demands is a necessity of great importance.

In the broader context of radiation therapy, a necessary precondition for treatment is the safeguard of patients and personnel from accidental radiation exposure. In particular, at proton beam treatment facilities, accidental exposure to beam radiation or derivatives thereof is perceived to be the principal threat to patient and personnel safety. Inadvertent exposure to radiation may for example occur through beam misdirection or improper timing of radiation beam delivery. Nevertheless, as the demand for proton beam therapy increases and treatment facilities become more complex, as for example at the Loma Linda University Medical Center, beamline safety becomes a premium and the challenge of insuring beamline safety is taken very seriously.

SUMMARY OF THE INVENTION

A preferred radiation treatment facility in accordance with the present invention basically comprises a radiation beam source, a plurality of radiation beam treatment locations, and a multiplexed switchyard and beam transport system for directing the radiation beam to a selected one of the radiation beam treatment locations. One potential problem associated with such a treatment facility is the possibility of accidental radiation exposure through wrong-path or multiple path activation. Thus, it is one object of the present invention to safeguard against accidental radiation exposure, as well as other hazardous conditions for personnel and apparatus.

In accordance with one aspect of the present invention, a method of radiation beam security comprises first receiving a beam request signal from a selected treatment location. A beam path configuration signal is derived from the beam request signal and used to select the switchyard and beam transport system configuration. The configuration of the switchyard and beam transport system is sensed to verify that the switchyard and beam transport system configuration allow radiation beam transport to the selected treatment location and no other. Upon verification of correct system configuration, radiation beam transport is provided to the selected treatment location.

Because there is a plurality of available beam paths, it is not only necessary to check that the selected path is activated, but preferably also that no additional beam paths are simultaneously active. The method of the present invention accomplishes this verification by deriving a switchyard and beam transport system configuration signal from the sensing procedure. The switchyard and beam transport system configuration signal is compared to the selected beam path configuration signal. This comparison entails verifying that every element of the selected beam path configuration signal is contained in the switchyard and beam transport system configuration signal, thus insuring that the selected path has been activated. The comparison further entails verifying that every element of the switchyard and beam transport configuration signal is contained in the selected beam path configuration signal, hence also insuring that no additional path is activated.

In addition to path configuration sensing, a preferred beamline control and security system safeguards against other hazardous conditions for personnel and apparatus such as electrocution, apparatus overheating and communication link failures. Sensing is preferably also performed to detect potential human contact with electrical load bearing components which may pose a threat of electrocution. Furthermore, sensing is preferably performed to detect over heating by electrical load bearing components. Communication failures are reduced by providing redundant communication paths for sensed information as well as signal processing steps. When redundant communication paths are mutual logical complements, their logical comparison provides a method to determine a communication link failure.

In accordance with another aspect of the present invention, an apparatus for radiation beam security comprises a means for receiving a beam request signal from a selected treatment location and a means for deriving a beam path configuration signal from said beam request signal, such as for example a digital signal communication network and local digital processor. The apparatus also comprises a means for selecting the switchyard and beam transport system configuration based on the selected beam path configuration signal. Furthermore, there is a means for sensing the configuration of the switchyard and beam transport system to verify that the switchyard and beam transport system configuration allow radiation transport to only the selected treatment location. Finally, there is means for providing radiation beam transport to the selected treatment location, in response to the aforementioned verification.

In accordance with another aspect of the present invention, an apparatus for controlling the multiplexed switchyard and beam transport system comprises a plurality of groups comprising elements of the multiplexed switchyard and beam transport system, wherein each group has a common functional characteristic different from the other groups. The apparatus further comprises a dedicated controller for each of the groups having a common functional characteristic. Preferably, each group comprises elements having a common functional characteristic pertaining to the transport of radiation to each of the plurality of radiation beam paths. Furthermore, preferably each dedicated controller operates to activate the respective functional elements for the selected beam path.

BRIEF DESCRIPTION OF THE DRAWINGS

FIGS. 3A and 3B are functional block diagrams of the switchyard magnet control system;

DETAILED DESCRIPTION OF THE PREFERRED EMBODIMENTS

Generally speaking, the beamline control and security system of the present invention is useful in a radiation therapy facility comprising a radiation beam source and a plurality of beam configurations through which the radiation beam may be directed. Such a therapy system is fully disclosed in U.S. Pat. No. 4,870,287 by Cole et al. and herein schematically illustrated in FIG. 1.

Figure 1:
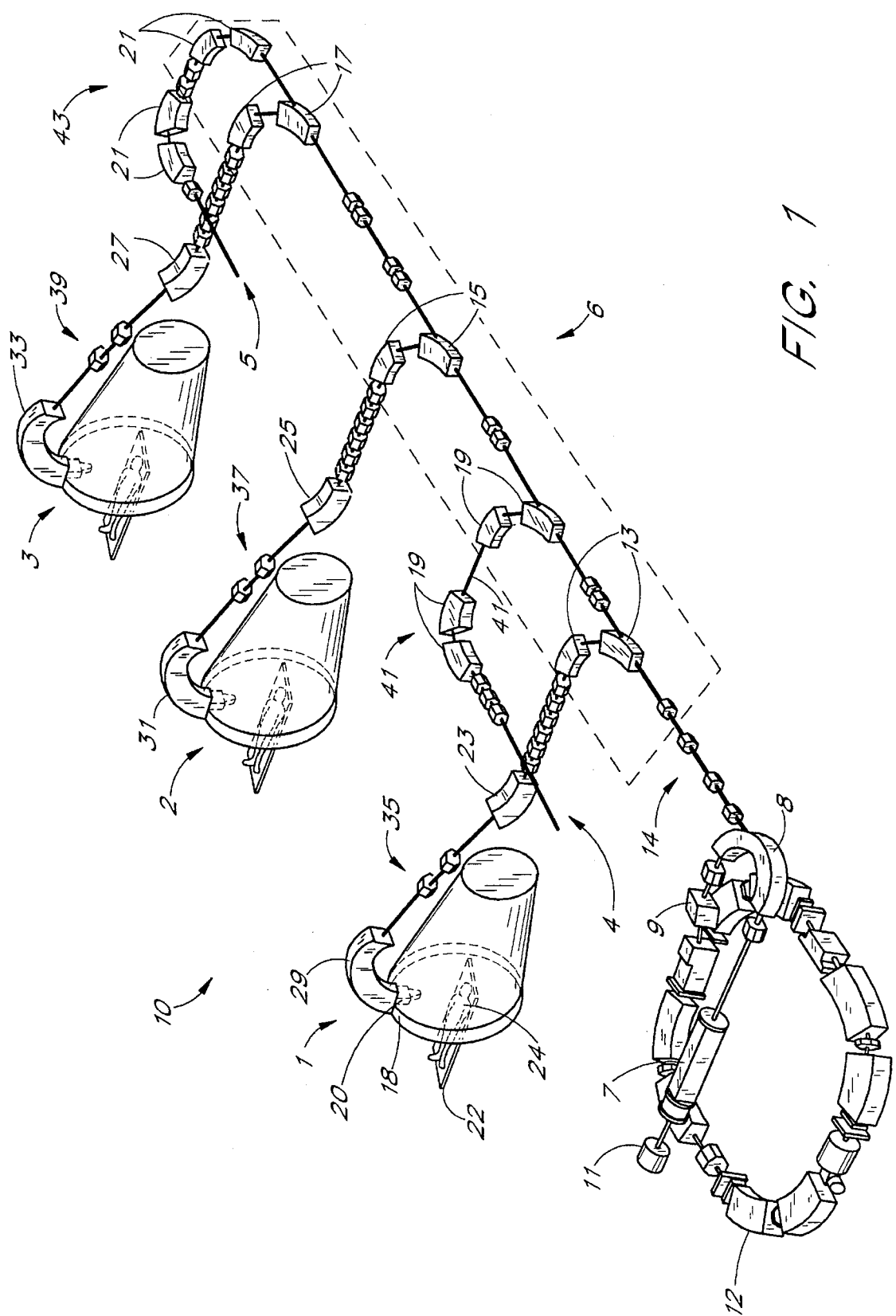
FIG. 1 is a schematic perspective of an exemplary proton beam treatment facility for which the present invention is particularly suited.

As depicted in FIG. 1, a proton beam therapy system 10 which may incorporate the present invention comprises a proton source 11 connected to an accelerator 12 by an injector 9. The proton accelerator 12 is connected to a beam transport system 14 which delivers the high-energy proton beam to patients 22 supported in fixed orientations in selected ones of a plurality of treatment stations 1, 2, 3, or for example to a fixed beam station 4 or research beam station 5. At each of the treatment stations 1, 2 and 3, the beam transport system 14 includes gantries 18, which are rotatable about an axis of rotation and carry beam optics for receiving a proton beam on its axis of rotation, transporting the proton beam away from the axis of rotation and directing the proton beam on a path perpendicular to and intersecting the axis of rotation. The intersection point is configured to be a target isocenter 24 within a patient 22 supported in a fixed orientation by a patient support, such as table. Thus arranged, upon a rotation of the gantry, the proton beam is delivered to the target isocenter 24, by delivery system 20 from several different angles during patient treatment.

More specifically, in the construction of the illustrated proton beam therapy system, conventional components are utilized, combined, adjusted and fine-tuned according to well known charged particle beam transport, acceleration and focusing techniques to achieve the accelerator and injection system parameters desired and the performance specifications and parameters. See, for example, those listed in Appendix I, Appendix II and Tables I–VIII of U.S. Pat. No. 4,870,287. As there listed, the source 10 may comprise a duoplasmatron ion source providing a 40 keV proton beam. The beam is focused by solenoidal lenses to match the beam into a radio-frequency quadrupole linear accelerator (RFQ) 7. The RFQ accelerates protons to 1.7 MeV for transmission through a 180 degree bending magnet 8 and subsequently through the injection septum 9. The injection septum 9 launches the proton beam into the accelerator 12. The accelerator 12 is a proton synchrotron capable of accelerating the injected beam to approximately 250 MeV in about 0.5 seconds, thus requiring an energy gain of about 90 eV per round trip. The beam is slow extracted from the synchrotron by horizontal half-integer resonant extraction or "spill," thereby introducing proton beam spills into the beam transport apparatus. The details of the synchrotron and its operation are more fully disclosed in U.S. Pat. No. 4,870,287.

The illustrated beam transport system 14 also includes a switchyard 6 comprising five switching magnets 13, 15, 17 and 19. Each switching magnet is characterized by two states and is electronically switchable between its two states in response to operator control. In the first state, switching magnet 13, for example, will receive the proton beam from the accelerator 12 and bend and deliver the proton beam to the downstream magnets and beam optics associated with the gantry 18 of the treatment station 1. In the second state, switching magnet 13 will pass the proton beam to the switching magnet 19 which in its first state will bend and deliver the proton beam to components in the beam stationary beam treatment station. In the second state for the switching magnet 19, it will pass the proton beam to the switching magnet 15. Like switching magnet 13, when switching magnet 15 is in its first state it will bend and direct the proton beam to the magnets and beam optics associated with the gantry 18 of treatment station 2. In its second state, switching magnet 15 will pass the proton beam to the switching magnet 17 which in its first state will bend and deliver the beam to the magnets and beam optics associated with the gantry 18 of treatment station 3. In its second state the switching magnet 17 will pass the beam to a magnet 21 for bending and direction to a beam research station 5.

As described above, the beam transport system 14 includes the switchyard 6 and the beam transport apparatus leading to treatment stations 1–3, as well as stations 4–5. The switchyard 6 includes the switching magnets 13, 15, 17, 19, 21 and the intermediate quadrupole magnets, also illustrated in FIG. 1. In passing from the accelerator 12, the beam is directed through four quadrupoles to the switching magnet 13, the general function of which has been previously described. All of the switching magnets are substantially the same in structure, function and control. Accordingly, only the switch magnet 13 will be described in more detail. The switching magnet 13 may be a 45° bending magnet, also referred to as SY45 magnets. The SY45 magnet is an electromagnet configured to bend a beam of protons of a specified momentum (energy) through an angle of 45° when current in a coil of the magnet is controlled to a precise current required for that momentum. When the magnet is not so energized, the protons proceed in a straight line through a hole provided in the yoke of the magnet to the next energized SY45 magnet. The control of the magnet is achieved by either (i) a contactor which turns on a direct current power supply and concurrently sends a digitized current setting to the power supply to require the supply to regulate at a prescribed current, or (ii) opening the contactor to turn off the supply. The controls are initiated by a control computer which initiates digital commands to a power supply interface (described later). The structure, function, and control of the SY45 magnets 13, 15, 17, 19, 21 are substantially similar. As disclosed herein, a single power unit is preferably switched between the SY45 magnets in response to the beam configuration request signals.

The 45° gantry bending magnets 23, 25, and 27 are located on the beam path at the head of each gantry 18 at treatment stations 1, 2, and 3, respectively. The 45° gantry bending magnets 23, 25, and 27 are configured to bend a proton beam through an angle of 45° when the magnet is energized. The gantry magnets 23, 25, and 27, also referred to as G45 magnets, have substantially the same structure, function, and control. They are preferably controlled by a single power unit, whereby electrical power is switched between the G45 magnets in response to beam request signals.

As is apparent from FIG. 1, each of the G45 magnets 23, 25, and 27 deflects the proton beam along paths 35, 37, and 39 adjacent to the respective treatment station gantries 18. The beam paths 35, 37, and 39 transport the beam to respective 135° gantry bending magnets 29, 31, and 33, also called G135 magnets. The G135 magnets deflect the proton beam through an angle of 135°, and thereby transport the beam to beam delivery systems 20 located in each gantry 18. The structure, function, and control of the G135 magnets 29, 31, and 33 are substantially the same. They are preferably powered by a single power source which is switched between the G135 magnets in response to beam configuration signals.

The following description discloses the basic design concepts and functioning of the dipole switch control system. It further discloses the preferred design and general requirements for performance.

A. Basic Control Structure

Figure 2:
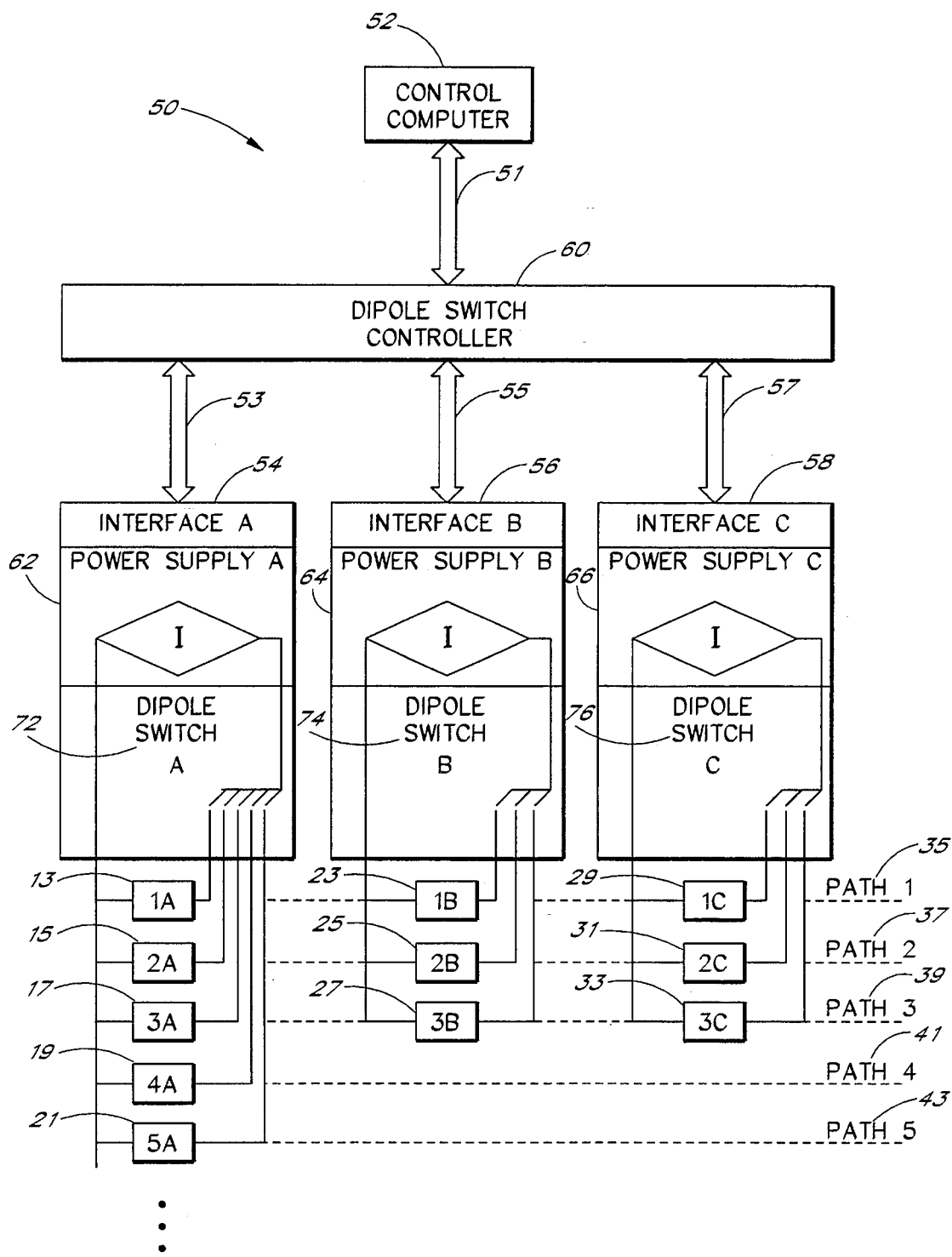
FIG. 2 is a simplified block diagram of the dipole switch control system.

The array of electromagnets comprising the proton beam deflection and control system is controlled in an arrangement such as illustrated in FIG. 2. Generally speaking, the array of switchyard and deflection magnets is multiplexed into a control system wherein magnet control is grouped or ganged in accordance with the function, control, and position with respect to various beam paths. Multiplexing the beamline magnets in this fashion provides simple, cost-effective, and safe beam configuration and control. As shown in FIG. 2, the proton beam control system comprises principally a control computer 52 connected to a Dipole Switch Controller (DSC) 60 which serves as the central component for the monitor and control system. The DSC 60 is connected to a plurality of dipole switch and power supply interfaces A 54, B 56 and C 58. The interface A 54 is connected to a magnet power supply A 62, having an output switched by the dipole switch A 72. A dipole switch is generally a multiple pole switch capable of directing a high-current electrical signal to a plurality of possible connections. A dipole switch may for example comprise a plurality of silicon controlled rectifiers (SCR) switches arranged to direct a high-current input into one of a plurality of output connections. In a similar manner, interface B 56 is connected to power supply B 64 and dipole switch B 74, and interface C 58 is connected to power supply C 66 which is connected to dipole switch C 76. The power supplies 62, 64, and 66, along with their respective dipole switches 72, 74, and 76, are configured to control the beamline magnet array such that magnets of a given type and function are powered individually by the same power supply. For example, power supply A 62 is configured to energize any one of the switchyard magnets 13, 15, 17, 19, and 21 through the selection of dipole switch A 72. Similarly, power supply B 64 is configured to energize any one of the 45° gantry magnets 23, 25, and 27 through selection of dipole switch B 74. Furthermore, the 135° gantry magnets 29, 31, and 33 are powered and controlled by power supply C 66 and dipole switch C 76.

In operation, a beam request is provided by control computer 52 and transferred to the dipole switch controller via interface 51. The dipole switch controller 60 encodes the beam request address into digital command signals specifying the selected dipole switch positions. Switch instructions are transferred via the interfaces 54, 56 and 58. The instructions are communicated to both the power supplies and the switches so that the switches are connected in the preselected orientations, and the respective power supplies enabled.

The orientation and operation of the beamline magnets in the aforementioned fashion is advantageous because the beamline magnets performing substantially similar functions with respect to the proton beam often require substantially the same operating conditions. For example, the 45° switchyard magnets will, in general, require similar operating power. Thus, power supply 52 supplies power for any one of the 45° switchyard magnets. Similarly, power supply 64 supplies the power for any one of the 45° gantry magnets, and power supply 66 supplies the power for any one of the 135° gantry magnets. The multiplexed arrangement reduces the number of very expensive power supplies needed to serve the treatment facility. Second, the aforementioned multiplexed arrangement reduces the number of components requiring monitor and control. In accordance with this scheme, a path address such as paths 1–5 (35–43) is decoded into various switch positions, whereby a path is selected by selecting simultaneously the desired switch position for dipole switches 72, 74, and 76. For example, the path 35 may be selected by selecting the switch position for dipole switches 72, 74, and 76, thereby engaging magnets 1A (13), 1B (23) and 1C (29). The dipole switches should be capable of switching and maintaining large electrical currents. They are preferably comprised of Silicon Controlled Rectifiers (SCR), whose composition and operation is well known in the art of high-power electronics.

B. Control System Functional Overview

The dipole switch control system interprets and directs proton beam steering commands from either a user- or computer-based supervisory platform to the silicon controlled rectifier (SCR) switches which steer current from the various magnet power supplies to the various dipole magnets, thereby directing the beam into one of a plurality of possible delivery areas. A primary concern governing the dipole switch control system design is safety. The first priority is the protection of personnel in and around the treatment area; and the second priority is the protection of the equipment itself from improper or destructive operating conditions. As will become clear in the present disclosure, these priorities are achieved through a system and associated hardware that provides a high margin of safety from a multiplicity of anticipated hazards. Thus, in addition to selecting a given path as described in connection with FIG. 2, a network of sensors and operations is employed to detect component or system failures. All status information concerning the dipole magnets, dipole switches, power supplies, and communication lines is communicated to the dipole switch controller (DSC) 60 by the communication lines 53, 55, and 57, as depicted schematically by the double-tipped arrows of FIG. 2.

Figure 3B:
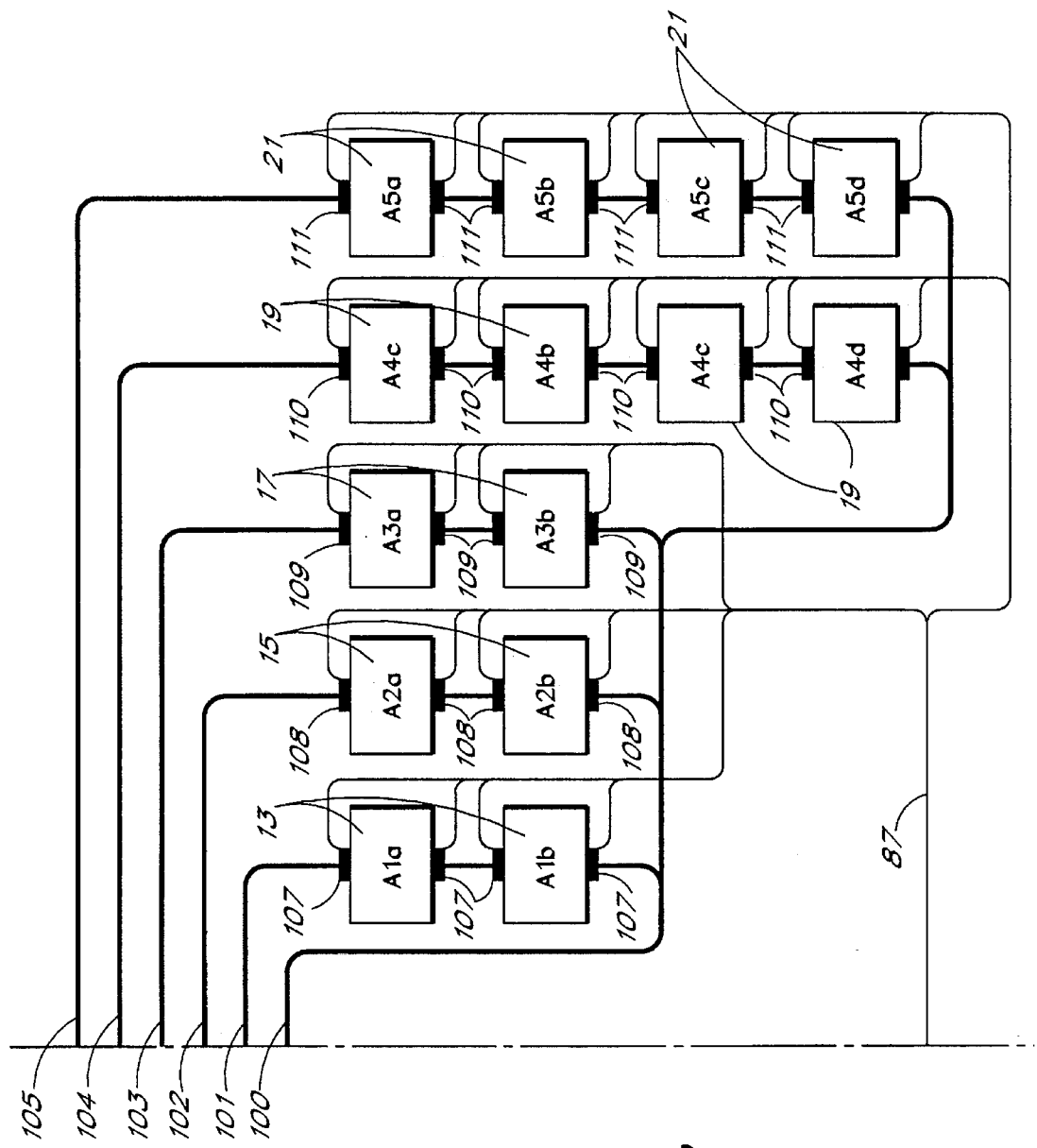
Figure 4:
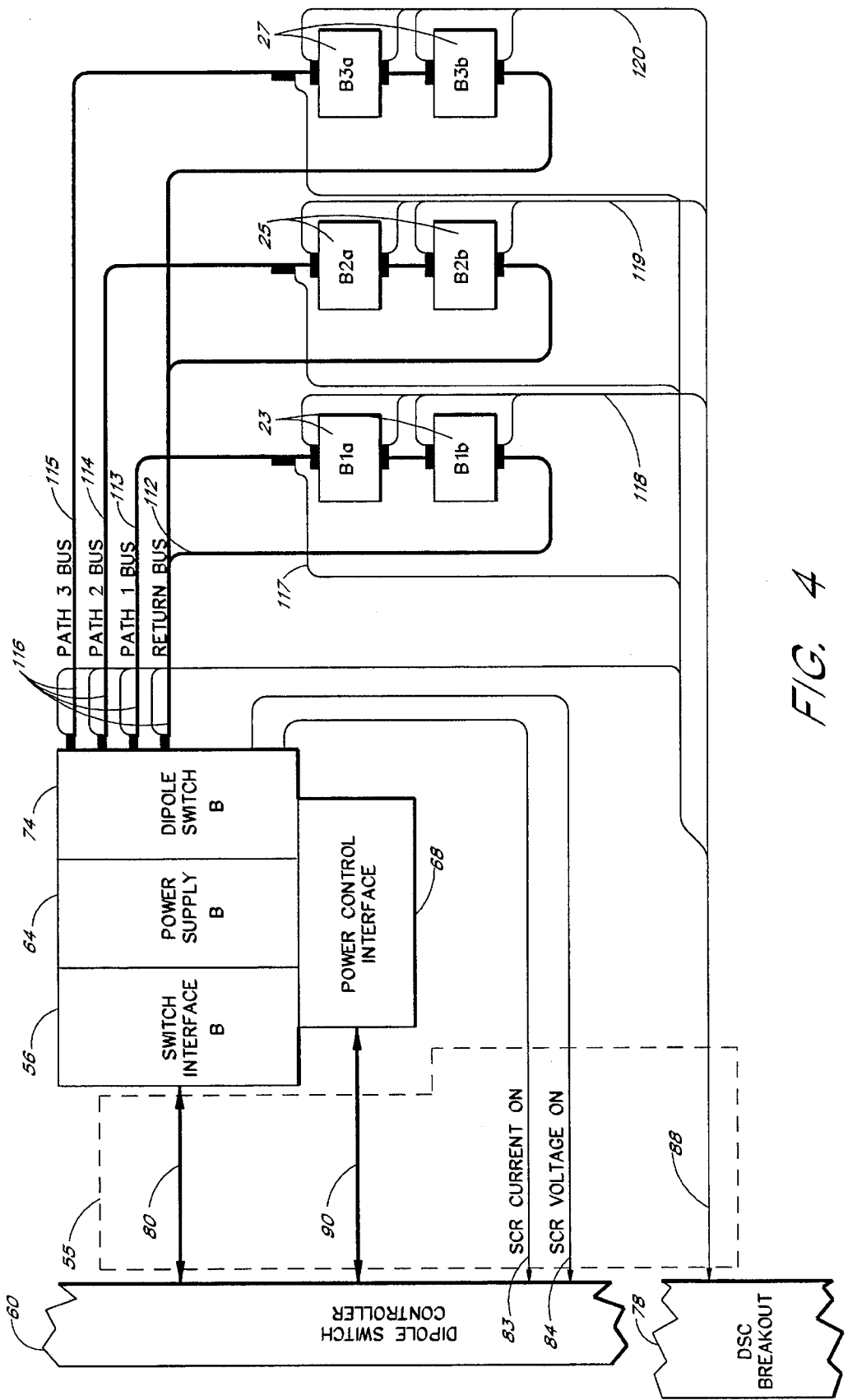
FIG. 4 is a functional block diagram of the 45° gantry magnet control system.
Figure 5:
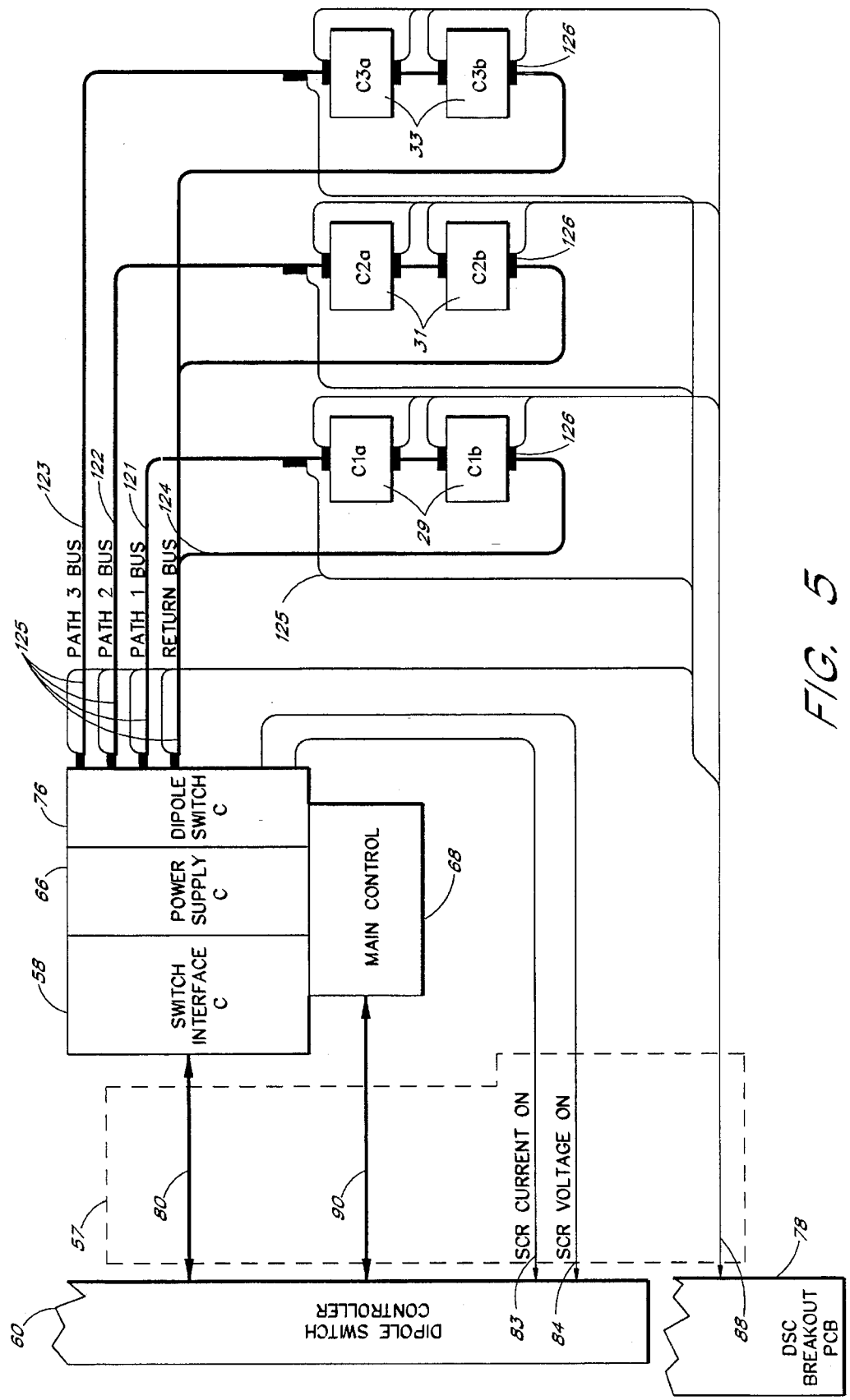
FIG. 5 is a functional block diagram of the 135° gantry magnet control system.

As shown in greater detail in FIGS. 3–5, the present exemplary embodiment of a dipole switch control system comprises a network of system monitor capabilities which are designed detect a plurality of possible system errors. In the event of such errors, the dipole switch control system disables the magnet power supplies, thereby preventing the proton beam from being transported in the event of a beam line component failure. Beginning with FIG. 3A which illustrates the functional components relating to the switchyard magnet control, the central components to the system comprise the system computer 52, DSC 60, power supply 62, and dipole switch 72, as previously described in connection with FIG. 2. The two-way communication link 61 between the DSC 60 and computer 52 includes such signals as path select addresses, status signals, and emergency shutdown signals. The control computer 52 is also connected to communicate with both the DSC 60 and the selection verification board (SVB) 70, which is disclosed in U.S. Pat. No. 5,260,581 and herein incorporated by reference. The DSC 60 supplies the SVB 70 with the dipole switch status information via communication line 71, and the SVB 70 in turn provides a safety interlock signal based on the analysis of switch status information. The principal connection between the DSC 60 and the beam line components, such as magnets, power supplies and switches, is made via the dipole switch interface 54 and power control interface 59. As shown in more detail in FIG. 3A, the two way communication link 53 of FIG. 2 comprises signals communicated between the DSC 60 and each of the dipole switch interface 54, power control interface 59 dipole switch 72 and dipole magnets. As previously mentioned, the DSC 60 transmits the beam path configuration signals to the dipole switch interface 54. In the present exemplary embodiment, the beam request signals 80 comprise, for example, a beam path address signal, address parity signal, and a path enable or strobe signal. The dipole switch status is monitored by current and voltage sensors located at each SCR (not shown) within the dipole switch 72. These current and voltage sensors supply the DSC 60 with signals 83 and 84 which indicate the SCR current and voltage, respectively. The SCRs are also preferably equipped with temperature sensors, which signals 88 are supplied to the DSC 60 as an indication of possible overheating. The DSC 60 also preferably receives path select error signals and parity error signals, which indicate possible communication fault conditions.

In concert with the path selection process and status signals, the DSC 60 will provide the power control interface 59 with signals to either disable or energize the supply via communication link 90. If path selection is implemented (by the DSC) and verified (by the SVB), then an output enable signal is conveyed to the interface 59. If any one of a number of fault conditions is detected, then an interlock signal is conveyed, disabling the power supply. In return, the power control interface 59 returns with an output status signal via communication link 90, informing the DSC that it is presently sourcing power. In the event of an emergency, a shutdown is executed by a shunt trip signal, which disables all three power supplies. Additionally the DSC receives status signals from the power supplies comprising a power supply contactor signal and gating signals.

As described previously in connection with FIG. 2, the dipole switch 72 primarily comprises an array of SCR switches. As shown in FIG. 3A, the SCR switches direct the electrical power supplied by power supply 62 to any one of a plurality of path current buses indicated by the dark lines 101, 102, 103, 104 and 105, which lead to the magnets shown on FIG. 3B. Thus, current from the supply is directed to any one of paths 1–5, each of which leads to the respective dipole magnets shown in FIG. 3B. The magnets share a common return bus 100. The current buses 100–105 carry the energizing current necessary for any one of the switchyard magnets. Since the buses 100–105 carry high electrical current to the magnets, they are subject to potential overheating, and therefore are supplied with bus temperature sensors 106 shown in FIG. 3A. The temperature information is supplied to the error detection circuit of the DSC 60 by the DSC breakout 78 as a bus temperature signal. The dipole magnets are also individually equipped with temperature sensors, as shown in FIG. 3B, by temperature sensors 107, 108,109, 110 and 111. The magnet temperature information is supplied to the DSC breakout 78 as a magnet temperature signal. Additional safeguards from possible overheating may include coolant flow monitors which sense the coolant flow for the current carrying magnets, which signals are also supplied to the DSC 60 as flow sensor signals. Also, while in operation, personnel are forbidden to enter potentially hazardous areas such as the switchyard magnet area. Unauthorized entry into such areas is secured with door interlocks 95, leaving signals that are supplied to the DSC 60. Bus temperature, magnet temperature and flow sensor information is supplied to a portion of the DSC 60 referred to as the DSC breakout PCB 78. A command from the DSC breakout PCB 78 may be issued to the main portion of the DSC 60 via link 97 to report any one of a number of fault conditions, including bus temperature, magnet temperature, flow sensor and unauthorized entry information. In response to these errors the DSC 60 will remove an interlock signal to the power supply interface 59, which disables the power supply.

Substantially analogous to that shown in FIGS. 3A and 3B, FIG. 4 is a functional block diagram illustrating the relationship between the dipole switch controller 60 and the components relating to the 45° gantry magnet control for paths 1, 2, and 3. Similar to the status and control system for the 45° switchyard magnets shown in FIGS. 3A and 3B, the 45° gantry magnets are controlled and monitored by the dipole switch controller 60. In operation, the dipole switch controller 60 supplies address signals, parity signals, and enable signals to the switch interface, which commands the dipole switch to direct electrical power from power supply 64 to the appropriate path bus 113,114, or 115. In return, the SCRs of dipole switch 74 are monitored by current signals 83 and voltage signals 84. The power supply 64 is enabled upon verification of the correct path implementation, as described previously. In the event of thermal errors, communication errors or path selection errors, the interlock signal is removed from the power supply interface 68 which disables the power supply 64.

Similar to the functional components and relationships outlined in FIG. 4, FIG. 5 illustrates the analogous components pertaining to the 135° gantry magnet control and monitor subsystem. The DSC 60 is connected to communicate with both the dipole switch interface 58 and power supply interface 68. The switch interface and power supply interface 68 are in communication with the dipole switch 76 and power supply 66, respectively. The dipole switch 76 is connected to direct electrical power from power supply 66 to any one of a plurality of 135° gantry magnets 29, 31 and 33 via current busses 121, 122 and 123. The 135° gantry magnets share a common return bus 124. Temperature sensors 125 are connected to each of the current busses 121–124. Additionally, magnet temperature sensors 126 are connected to the 135° gantry magnets 29, 31 and 33.

The operation of the subsystem shown in FIG. 5 is analogous to the operation of subsystems shown in FIGS. 3 and 4. The switch interface 58 receives and decodes path address signals and path select signals from the DSC 60, and further relays such information to the dipole switch 76. When the path selection corresponding to the selected dipole switch positions is verified, then a power supply enable signal is supplied to the power supply 66. Status signals provided to the DSC 60 include temperature sensor signals originating from the dipole switches, current busses and magnets; as well as communication error signals originating from special detector circuits as well as complimentary redundant logic checks (described later). Switch status is communicated by the dipole switch sensor signals 83 and 84 which relay current and voltage information pertaining to each of the SCRs in the dipole switches. Temperature sensor signals, as well as other error sensing signals, are supplied to the DSC 60 through the DSC breakout PCB 78. If one of the signals becomes active, the DSC will initiate a partial or complete system shutdown through a safety interlock signal.

Figure 6:
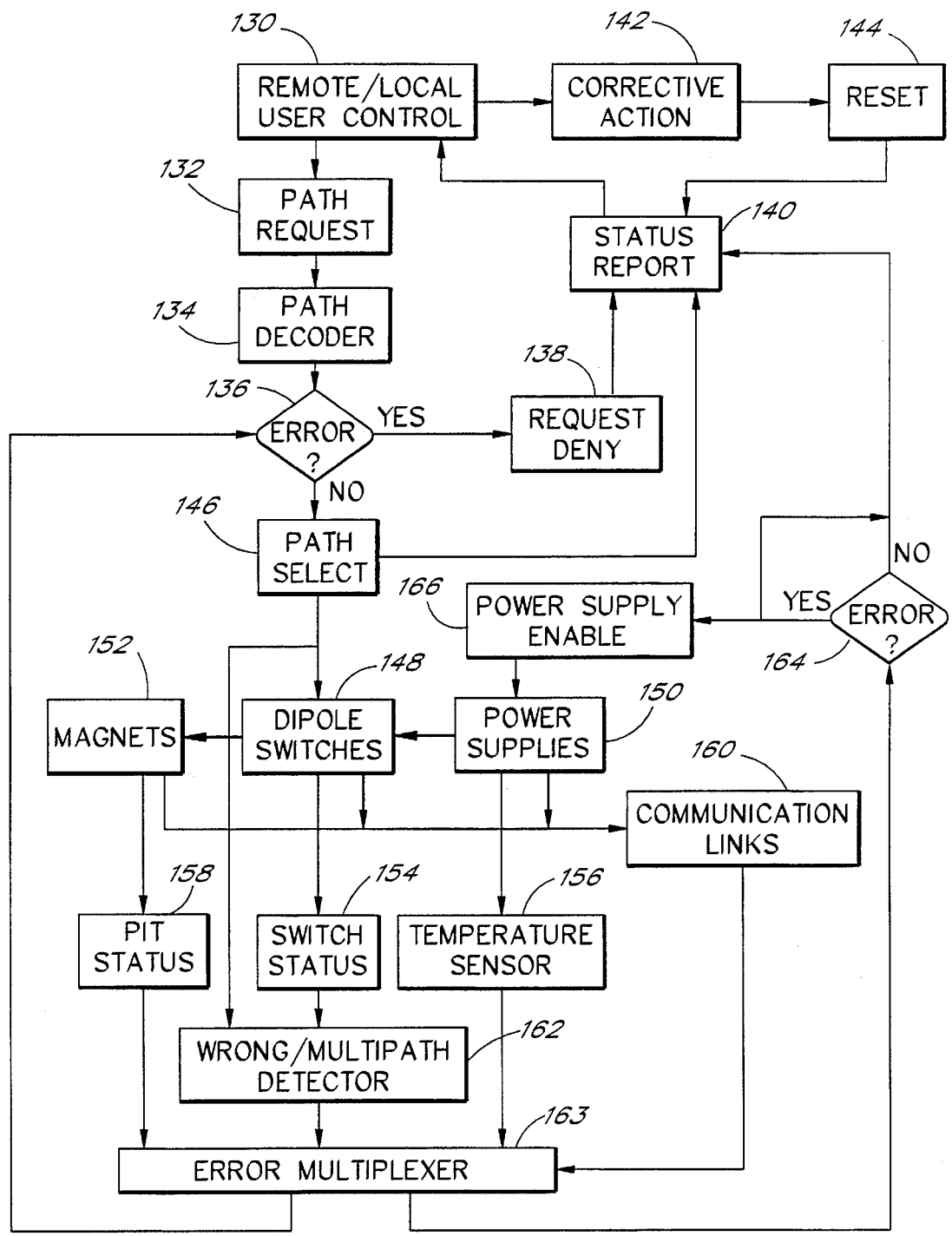
FIG. 6 is a basic flow diagram of the dipole switch control system.

A simplified flow diagram for a basic embodiment of a preferred beamline control system is shown in FIG. 6. Through either remote or local process control 130, a user executes a path request action 132, comprising transmitting an encoded path address and path request signal to the DSC 60, shown previously in connection with FIGS. 2, 3, 4 and 5. The path request signal is received by the DSC 60 and decoded in process block 134 into the individual switch position addresses corresponding to beam paths 0–5, where path 0 represents a null path, and paths 1–5 correspond to those previously outlined in connection with FIG. 1. A path request signal which has been received and decoded by the DSC 60 initiates an error and status examination, as indicated by decision block 136. In the event an error condition exists, the path request is passed onto the path request deny block 138 which freezes all switch positions and executes a status examination in process block 140. The system status and error conditions are passed onto the user through which corrective action and reset functions are executed, as indicated by process blocks 142 and 144, respectively. When the error conditions have been corrected and the dipole switch controller has been reset, the user is then free to re-execute a path request, as previously outlined. Returning, to the status examination and error block 136, if no errors are found, a path request is passed onto a path select process block 146 which sends the appropriate dipole switch configurations to each of the dipole switch interfaces, as well as to a wrong/multipath detector 162. When a switch selection has been made, switch status information, originating at the dipole switch SCRs, is passed onto a wrong/multipath error detector 162. If no path error is detected, then a command is relayed to a power supply enable/disable process to allow power to be directed to the dipole magnets, indicated by the solid dark arrows extending from the power supplies 150 through the dipole switches 148 and to the dipole magnets 152. If a path error is detected, then a signal is sent to the error evaluator 164 which removes the power supply enable function 166, thereby preventing magnet power up. In addition to the multipath and wrong path detection, other safeguards include pit status monitoring, wherein a safety interlock is triggered upon entry into any of the lower gantry areas. If an unauthorized entry condition is detected, then a signal is transmitted to an error and status evaluator 164 which triggers the power supply emergency shutdown function 166, thereby disabling the appropriate magnet power supplies. Additionally, thermal sensors 156, disposed at the dipole magnets current bus locations, and dipole switches, as previously described, supply information to the over-temperature detectors. If an over-temperature condition exists, the power supply enable function 166 is removed. Furthermore, communication and interface errors are monitored by comparing path address with address parity, as well as parallel-complement link failures. If an error exists, then further path selection is halted. Selected error conditions will further cause the appropriate power supplies to be disabled.

C. Personal Protection Requirements

Two principal threats to personnel are believed to be present during the operation of the exemplary proton beam therapy facility. The first is proton irradiation due to misdirected or mistimed beam delivery, and the second is electrocution by accidental contact with potentially hazardous electrical potentials.

Figure 7A:
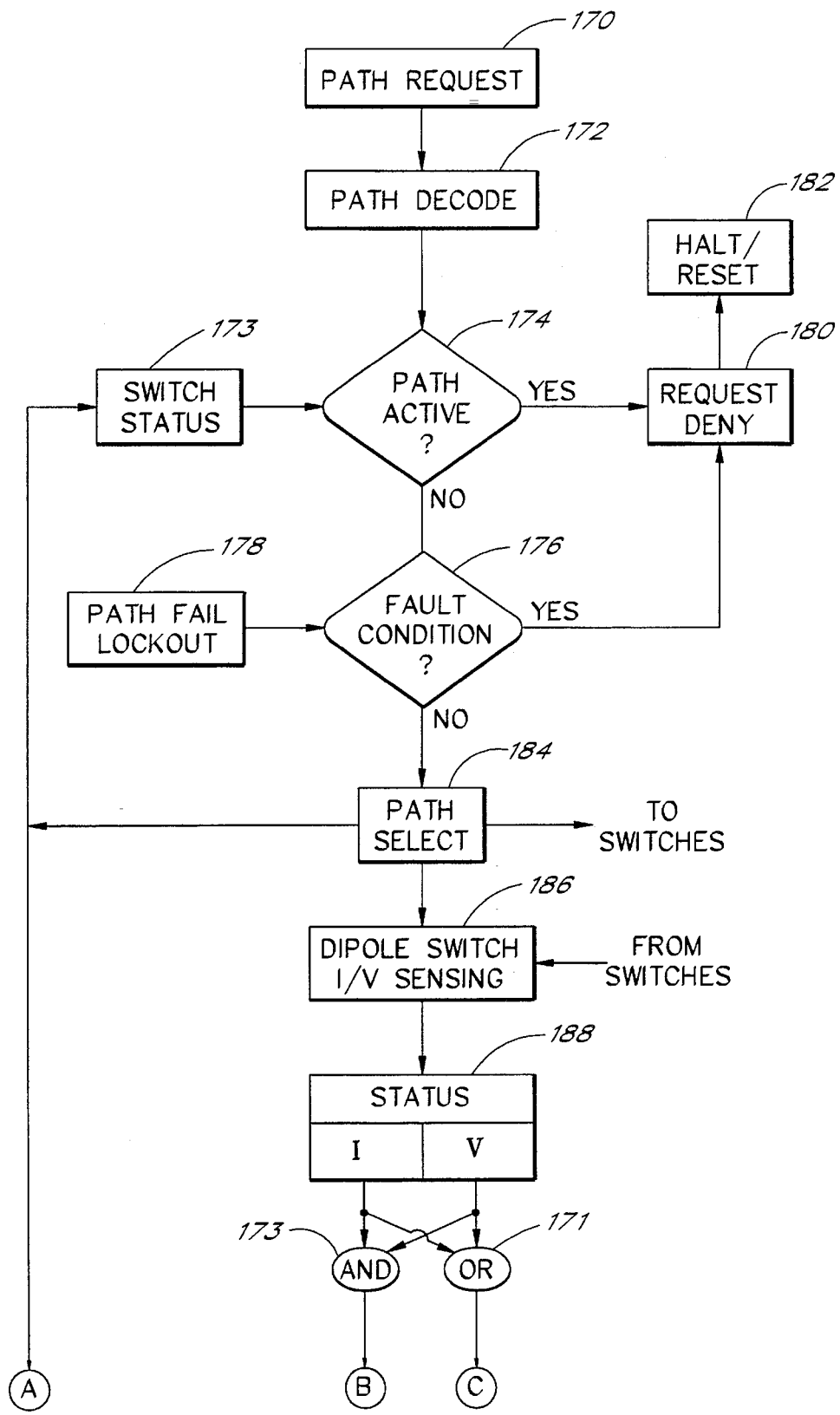
FIG. 7A–B is a simplified flow diagram of the proton beam control system safety features.

The dipole switch control system of the present invention provides safeguards against incorrect or multiple proton beam path activation. To prevent multiple path or wrong path activation, separate current and voltage sensors are employed for each of the dipole switch SCRs, located in the dipole switches 72, 74, 76. The current and voltage sensors are used to determine the state of each SCR of the dipole switch control system. A characteristic of SCR switches is that they may fail in the "ON" condition, or that they may turn "ON" unexpectedly due to electrical noise or spurious pulses. This could result in beam delivery to a wrong path or multiple paths. A preferred embodiment of the dipole switch control system prevents wrong and multiple path activation by continuously comparing the measured states of the dipole switches to the states of the dipole switches corresponding to the selected path, as illustrated in the simplified flow diagrams of FIGS. 7A and 7B. Referring first to FIG. 7A, the process of path selection and verification begins with a path request 170, typically initiated under computer control by an operator in one of the treatment rooms. The path request is decoded into a set of digital signals corresponding to the state of each dipole switch, indicated in FIG. 7A by the process block 172. In a first decision block 174, further path request processing is gated by the present path activity. If a path is currently active, then the path request is denied, as indicated by block 180, and further process control is routed to a halt/reset routine indicated by process block 182. If no path is currently active, then further processing of the path request is gated at decision block 176 by various fault conditions which may be hazardous to personnel and patients. For example, unauthorized entry into areas having lethal electrical power will initiate a path-fail fault condition, indicated by block 178. A facility user may also lockout or prevent a specific path from being selected, also indicated by process block 178. If a fault condition is determined to exist, then the path request is denied and processing is routed to a halt/reset routine indicated by block 182, as described earlier. When no fault is present, then the path is selected, as shown at process block 184; for example, by sending the appropriate electrical signals to each of the dipole switches. The path select information is also routed to a status buffer indicated by block 173 for system monitoring and to prevent additional path requests during a treatment session.

Figure 7B:
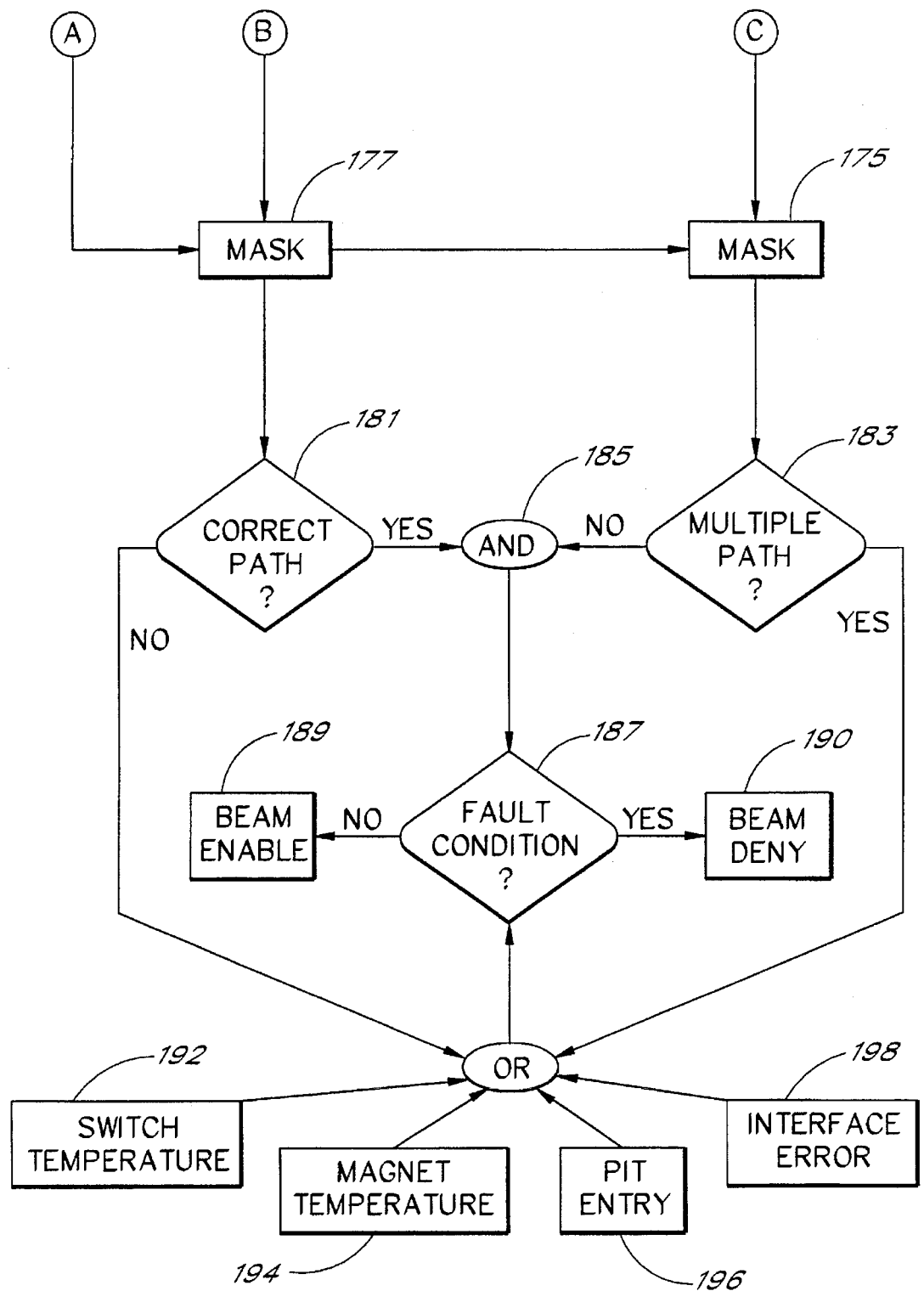

The aforementioned SCR current and voltage sensors monitor the state of each SCR, which information is received from the sensors, represented by process block 186, and routed to a switch status buffer 188, indicating both current I and voltage V information. The current and voltage state for each SCR of the dipole switches are logically ANDed to determine which switches are active, as indicated in process block 173. The information from process block 273 indicates which SCR switches are active and is passed on for correct path determination. Similarly, the current and voltage state of each SCR logically ORed to determine which SCR is conducting, as indicated in process block 171, and this information is used to determine wrong path or multiple path conditions. Referring now to FIG. 7B, the array of conducting SCRs determined by process block 171 is compared with the desired path at process block 175 to verify that only the correct path, and no other, is active. The active SCRs indicated by process block 173 are compared to the desired path at process block 177 to verify that all of the required magnets are energized before a proton spill is allowed. The latter operation is referred to as the method of selection verification which in the present exemplary embodiment is carried out by a selection verification process maintained in communication with the dipole switch controller. It will be appreciated that the dipole switch control system herein disclosed performs a complementary operation to that of the selection verification process disclosed in U.S. Pat No. 5,260,581, and herein incorporated by reference. In particular, the method of selection verification ensures that the desired beam configuration has been implemented before enabling beam transport. On the other hand, the present preferred switch control system performs switch status operations to ensure that no other switch is activated aside from the desired switches. Furthermore, the presently disclosed dipole switch control system actively disables beam transport components such as dipole magnet power supplies in the event of wrong or multipath errors. Thus, the present preferred embodiments operate in tandem with the selection verification process to ensure that the desired path, and only the desired path, has been selected.

The information from process blocks 175 and 174 is passed to respective decision blocks 183 and 181. At decision block 183, a multiple path check is carried out. If no path fault is detected, then an enable signal is passed on to process block 185. Similarly, at decision block 181 a correct path check is executed, and a corresponding enable signal is communicated to process block 185. Process block 185 comprises a logical AND operation, whereby a beam enable signal is activated if and only if there is a correct path selected and no multiple path exists. The beam enable signal is passed on to decision block 187, which comprises a fault determination process. If a fault is not detected at decision block 187, then the proton beam is enabled, as indicated by process block 189. If, on the other hand, any of a variety of fault conditions are present, for example, incorrect or multiple path selections, switch temperature 192, magnet temperature 194, pit entry 196, or interface error 198, then the proton beam request is denied, as indicated by process block 190.

Because SCRs have the characteristic of remaining latched ON as long as current flows through them, the DSC will not allow path selection to be made as long as any previously selected path is determined to be sourcing current. Preferably, a time delay circuit is implemented to allow residual currents which are below the detection threshold, to fall to zero. The delay period is typically about eight seconds. It does not begin until all current and voltage sensors are off and all output-on signals from the power supplies are off.

Each beam path and treatment area is provided with one or more emergency shutdown "mushroom" switches. These switches are both mechanically and electrically latched. Activation of a switch prevents that path from being selected until the fault is removed. If the path is active at the time the shutdown is requested, the power supply interlock fault is asserted to take the path supplies off-line. The fault is latched until the switch is restored mechanically and the latch is cleared by computer or local reset. To permit testing or maintenance of a particular portion of the beam delivery system, each path is provided with a manual lockout switch. Operating this switch disables the path for both local and remote control until the switch is returned to the normal position. Only the path in question is disabled; the remaining paths are available for use.

To prevent accidental contact with high power electrical apparatus, the dipole switches are located inside the power supply enclosures, and are protected by the supply access interlock system. Removal of a pit secure permit prevents the gantry path associated with that pit from being selected. If the gantry path is active at the time of violation, all supply interlock circuits are faulted to take the associated supplies off-line. The fault is latched until both the permit is restored and the latch is cleared by remote reset or local reset.

D. Equipment Protection Requirements

The primary threat to the dipole switch and the dipole magnets is perceived to be excessive heat, whether caused by overcurrent or by lack of coolant. In the present exemplary embodiments, there are a total of eleven SCRs in the three dipole switches: five in switch 72 and three each in each of switches 74 and 76. Each SCR has attached to it one or more thermally sensitive switches, preferably of the Klixon™ type. The Klixons in any given dipole switch are preferably wired in series, so that the overheating of an SCR will fail that switch, but not the other two switches. The Klixons are also preferably optically isolated from the DSC. The activation of any dipole switch thermal sensor will fail the entire dipole switch and power supply, but it will leave intact those portions of the path which connect to other switches, and it will not disable any other paths associated with the failed switch. Thermal faults are latched until the SCR has cooled and the latch is cleared by a reset signal.

To prevent dipole magnet thermal damage, each of the dipole magnets in the beam delivery system are equipped with one or more Klixon switches. The magnet Klixons are grouped two ways, by path and by dipole switch. The Klixons for the two 45° magnets of path 1 (gantry 1) on switch 72 are series-wired, as are the two 45° magnets of path 1 on switch 74, and similarly with the magnets of switch 76. The opening of any thermal switch will disable only the power supply and dipole switch associated with that magnet, but no other. Thus, the other magnets (if any) in the path will continue to operate. Only the fixed beam room path (path 4) and the calibration room path (path 5) will be totally disabled by a magnet Klixon actuation because all of the magnets for these paths are supplied by switch 72 and power supply 62. The Klixons are preferably optically isolated from the DSC 60. The activation of a dipole magnet thermal sensor activates the power supply interlock circuit to disable the power supply which powers that magnet. No other magnet or power supply in the associated path will be affected. The fault is latched until both the access violation is removed and the latch is cleared by a computer or local reset. Provision is made in the DSC for up to five flow sensor switch inputs, allowing for additional redundant safety feature. One flow sensor is allowed for each path. A flow failure has the same logical effect as a pit security violation for the affected path.

E. Reliability Requirements

Additional preferred aspects of the DSC design include fail-safe characteristics, testability and total status reporting. All DSC input and output circuits are designed to be fail safe. This means that no single-point failure in a communications path will allow an error condition to go undetected by the DSC. The most likely failure mode in a wired communications system usually involves mechanical degradation of the physical system itself: connectors becoming unmated, wire breakage due to abnormal stresses, shorts caused by abrasion or cuts to the installing medium, corrosion on connector pins, and similar defects. Preventive safeguards include control and error reporting signals that are configured such that the loss of the signal will automatically indicate an error condition to the DSC.

Figure 8:
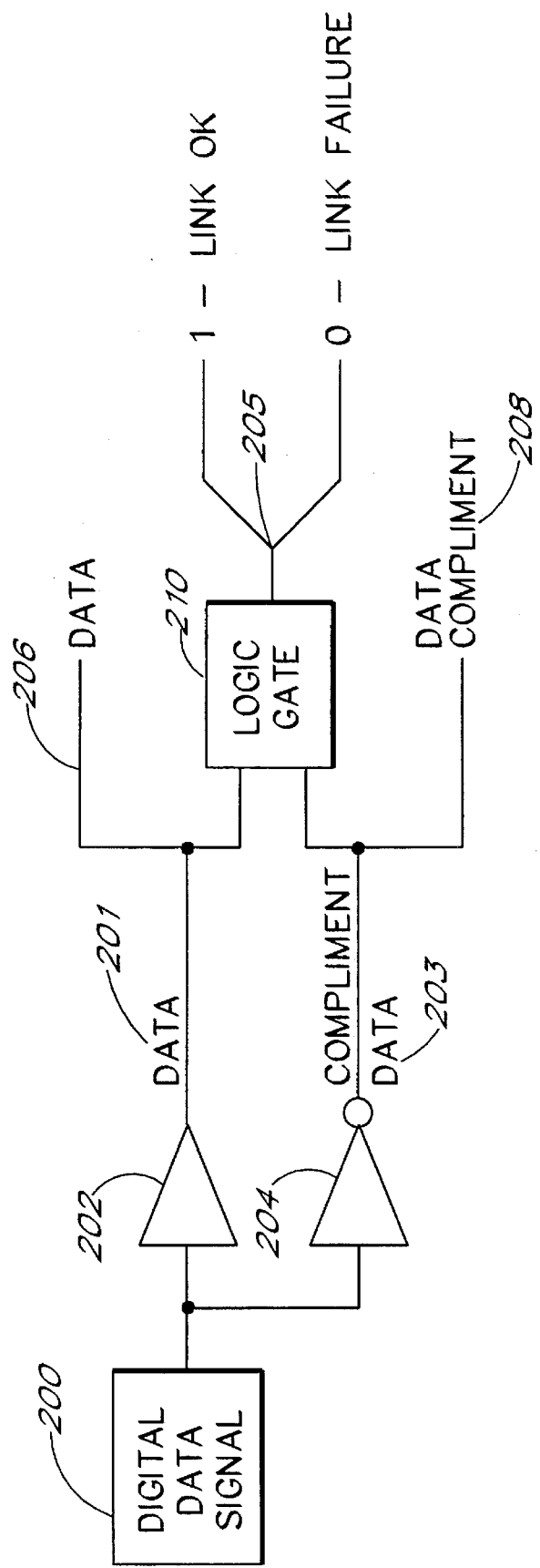
FIG. 8 is a simplified schematic of the complimentary redundant logic used throughout the system.

As shown in FIG. 8, a simplified functional representation of a fail-safe communication link may comprise a gating operation in which a data signal is gated by its logical complement. A digital data signal 200 is supplied to parallel but complementary unity gates 202 and 204. The unity gate 202 has an output 201 equal to the input data 200, while the unity gate complement 204 generates the signal 203 complementary to the input signal 200. Signals 201 and 203 are supplied to the logic gate 210, such as an exclusive OR gate, which generates a link status signal 205. If the link status 205 is high, then the link is operational; while if the link status 205 is low, then the link has failed. The above-described complementary redundant logic may be implemented in a variety of fault-sensitive signal arrangements, for example, at single point communication links, such as the thermal switches, current and voltage sensors, which provide communication redundancy. It can also be used to generate other complementary signal operations in a self-checking arrangement, such as path selection, multipath or wrong path detection, over-temperature detectors, and communication detectors. The implementation and use of complementary redundant logic elements, such as shown in FIG. 8, eliminates potential single point communication failures. They also provide redundant, self-checking functional elements at a variety of functional levels, which increases system reliability in a cost effective way.

Figure 9:
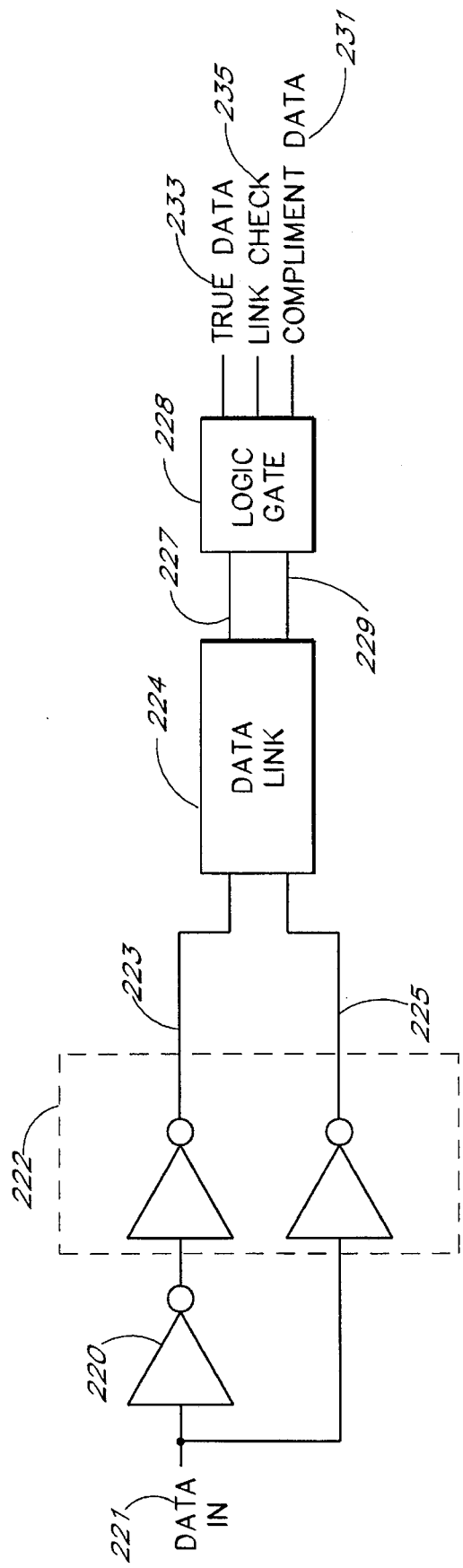
FIG. 9 is a schematic of complimentary redundant optical couplers.

The above-described complementary redundant functional characteristic is advantageously applied to increase the reliability of fault critical sensor links. For example, dual optical isolators are employed on fault critical signals, such as electrical and thermal sensor links. As shown in FIG. 9, a data signal 221, such as that generated by a sensor, is supplied to elements 220 and 222, which generates an identity signal 223 and a complement signal 225. The signal 223 and its complement 225 are supplied to a data link 224. The input signals 223 and 235 are preferably differentially connected to the data link 224 such that the data link outputs have opposite signal polarity. Hence, if one output is in a high state, the other output will be in a low state, generating complementary signals for every input combination. Complementary signals 227 and 229 emerging from the data link 224 are supplied to the logic gate 228, whose output signal 235 functions as a link status signal. The data signal 233 and complement 231 are passed to other DSC operations which may be executed in true and complementary forms for added reliability and status monitoring.

Special error detection circuits are used on signals such as DSC address lines, which have no "fault" condition (described later). This circuit configuration permits detection and reporting of partial or total communications failure. Additionally, DeMorgan equivalent parallel circuits are used on the thermal paths, where there would otherwise be no system redundancy to prevent single-point electrical component failures from masking a potentially disastrous condition.

Every input circuit of the DSC is equipped with at least one normally closed relay contact which may be opened under computer control to perform self-test. Self-testability is invaluable in the debugging process, and it is an important asset in establishing the reliability of safety-critical boards when it incorporated into power-up routines and daily or pre-use test programs. Thirty 4-pole double-throw relays are preferably used for this purpose, with additional relays reserved for future expansion. Every input to the DSC board is available to the host computer as a status bit. In the present exemplary embodiments, a total of 140 bits of status information is available. Eight of these bits represent major faults and are continuously available. The remaining 132 bits of secondary status are multiplexed under host control in 8-bit bytes. Several spare bits are provided to allow for future expansion. All error information is latched in the DSC and held for examination by the operator or the central computer's failure analysis program. A status sub-set is also displayed on the DSC front panel by light emitting diodes (LEDs).

The invention may be embodied in other specific forms without departing from its spirit or essential characteristics. The described embodiments are to be considered in all respects only as illustrative and not restrictive. The scope of the invention is therefore indicated by the appended claims rather than by the foregoing description. All changes which come within the meaning and range of equivalency of the claims are to be embraced within that scope.

We claim:

1. In a radiation beam therapy system comprising a radiation beam source, a plurality of radiation beam treatment locations, and a multiplexed switchyard and beam transport system for directing the radiation beam to a selected one of the radiation beam treatment locations, a method of radiation beam security comprising the steps of:

(a) receiving a beam request signal from a selected treatment location;

(b) deriving a beam path configuration signal from said beam request signal;

(c) selecting the switchyard and beam transport system configuration in accordance with said beam path configuration signal;

(d) sensing the configuration of the switchyard and beam transport system to verify that the switchyard and beam transport system configuration allow radiation beam transport to only said selected treatment location;

(e) in response to step (d), providing radiation beam transport to said selected treatment location; and (f) sensing the temperature of electrical load bearing components within said switchyard and beam transport system to determine an over-temperature condition; and (g) denying beam transport in the event of said over-temperature condition.

2. The method of claim 1, wherein step (d) comprises:

deriving a switchyard and beam transport system configuration signal from said sensing step;

comparing the switchyard and beam transport system configuration signal to said selected beam path configuration signal;

verifying that every element of the selected beam path configuration signal is contained in the switchyard and beam transport system configuration signal; and verifying that every element of the switchyard and beam transport system configuration signal is contained in said beam path configuration signal.

3. The method of claim 2, further comprising:

denying beam transport in the absence of verification of step (d).

4. The method of claim 3, further comprising:

sensing potential human contact with electrical load bearing components within said beam transport system and switchyard; and denying beam transport in the event of said potential human contact.

5. The method of claim 4, further comprising:

transmitting sensed information by redundant communication paths.

6. The method of claim 5, further comprising:

comparing said mutual logical complimentary redundant communication paths to determine a communication link failure; and denying beam transport in the event of said communication link failure.

7. The method of claim 4, wherein said redundant communication paths are mutual logical compliments.

8. The method of claim 6, further comprising:

comparing said switchyard and beam transport system configuration signal to said selected beam path configuration signal to determine a beam path error, in each of said logical complimentary redundant communication paths; and denying beam transport in the event of said beam path error.

9. The method of claim 2, further comprising:

transmitting said selected beam path configuration signal by mutual logical complementary redundant communication paths;

transmitting said switchyard and beam transport system configuration signal by mutual logical complementary redundant communication paths;

comparing said respective mutual logical complementary redundant communication paths to determine a communication link failure; and denying beam transport in the event of said communication link failure.

10. In a radiation beam therapy system comprising a radiation beam source, a plurality of radiation beam treatment locations, and a multiplexed switchyard and beam transport system for directing the radiation beam to a selected one of the radiation beam treatment locations, an apparatus for radiation beam security comprising:

(a) means for receiving a beam request signal from a selected treatment location;

(b) means for deriving a beam path configuration signal from said beam request signal;

(c) means for selecting the switchyard and beam transport system configuration in accordance with said selected beam path configuration signal by enabling a first set comprising less than all of a plurality of switchyard and beam transport elements wherein enabling said first set of elements provides a path for transport of said radiation beam to said selected treatment location;

(d) means for sensing the configuration of the switchyard and beam transport system to verify that (i) all of said first set of said switchyard and beam transport elements are enabled and (ii) all elements of said plurality of elements not in said first set are not enabled so that the switchyard and beam transport system configuration allow radiation beam transport to only said selected treatment location;

(e) means for providing radiation beam transport to said selected treatment location; and (f) means for interrupting said providing of transport to said selected treatment room in response to said means for sensing when an element not in said first set is enabled.

11. The apparatus of claim 10, wherein said means for receiving a beam request signal from a selected treatment location comprises a central control computer that receives said beam request signals.

12. The apparatus of claim 10, wherein said means for selecting the switchyard and beam transport system configuration is comprised of a switch controller and wherein said plurality of switchyard and beam transport components are comprised of switches which control magnets that steer said radiation beam.

13. The apparatus of claim 12, further comprising sensing means for sensing the state of said plurality of switches and wherein said switch controller receives signals from said sensing means indicative of the state of said plurality of switches.

14. The apparatus of claim 10, wherein said means for interrupting said providing of transport of said radiation beam to said selected treatment room interrupts said providing of said radiation beam in response to said sensing means sensing that one of said selected elements has become disabled during said beam transport.

15. In a radiation beam therapy system comprising a radiation beam source, a plurality of radiation beam treatment locations, and a multiplexed switchyard and beam transport system which comprises a plurality of beam paths for directing the radiation beam to a selected one of the radiation beam treatment locations along a selected beam path, a method of radiation beam security comprising the steps of:

(a) receiving a beam request signal from a selected treatment location;

(b) deriving a beam path configuration signal from said beam request signal indicative of a selected beam path for said radiation beam to said selected treatment location;

(c) selecting the switchyard and beam transport system configuration in accordance with said beam path configuration signal;

(d) sensing the configuration of the switchyard and beam transport system to verify that (i) the switchyard and beam transport system configuration allows radiation beam transport to said selected treatment location along said selected beam path and (ii) the switchyard and beam transport system configuration does not allow radiation beam transport along a non-selected beam path of said plurality of beam paths;

(e) in response to step (d), providing radiation beam transport to said selected treatment location;

(f) sensing the configuration of said beam transport system while radiation transport is provided to said selected treatment location; and (g) interrupting transport to said selected treatment location upon sensing that either (i) the configuration of said beam transport system allows radiation beam transport along a non-selected beam path of said plurality of beam paths or (ii) that said configuration of said beam transport system no longer allows transport to said selected treatment location.

16. The method of claim 15, wherein step (d) comprises:

deriving a switchyard and beam transport system configuration signal from said sensing step;

comparing the switchyard and beam transport system configuration signal to said selected beam path configuration signal;

verifying that every element of the beam path configuration signal is contained in the switchyard and beam transport system configuration signal; and verifying that every element of the switchyard and beam transport system configuration signal is contained in said selected beam path configuration signal.

17. An apparatus for providing radiation beam security for a radiation beam treatment system having a radiation source, a plurality of radiation treatment locations and a plurality of paths connecting said radiation source to said plurality of radiation treatment location, said apparatus comprising:

a plurality of switches having a first state and a second state wherein said plurality of switches are divided into a plurality of sets of one or more switches and wherein each set of switches directs said radiation beam along one of said plurality of paths when each of said one or more switches in said set are in said first state;

a plurality of sensors which provide signals indicative of the status of said plurality of switches; and a switch controller which receives said signals from said plurality of sensors and also receives a signal indicative of a desired beam path wherein said switch controller allows transport of said radiation beam by said radiation beam along said desired beam path to said radiation treatment location when both (i) said plurality of sensors indicate that a set of said plurality of switches corresponding to said desired beam path are in said first state and (ii) said plurality of sensors indicate that the switches in said plurality of switches that are not in said set of switches corresponding to said desired beam path are in said second state and wherein said switch controller monitors the signals from said plurality of sensors while beam transport occurs along said desired beam path and halts transport of said beam when said plurality of sensors indicate that one or more of said switches not in said set of switches corresponding to said desired beam path enters said first state.

18. The apparatus of claim 17, wherein said switch controller halts transport of said beam when said plurality of sensors indicates that one or more of said switches in said set of switches corresponding to said desired beam path enters said second state.

19. The apparatus of claim 17, wherein said radiation beam is comprised of a proton radiation beam and said plurality of switches are comprised of switching magnets having a first position and a second position which steer said proton beam along one of said plurality of paths in said first position.

20. The apparatus of claim 17, further comprising a plurality of dipole switches corresponding to said plurality of magnets each of said plurality of dipole switches having a first position and a second position which provide power to said switching magnets to induce said switching magnets to change between said first position and said second position.

21. The apparatus of claim 20, wherein said plurality of sensors sense the status of said plurality of dipole switches.

22. The apparatus of claim 21, wherein said plurality of dipole switches are comprised of SCR switches.

23. The apparatus of claim 17, further comprising a central computer that receives a beam request signal from a treatment location and provides a signal to said switch controller indicative of said desired beam path.

24. The apparatus of claim 23, wherein said central computer determines if said beam request signal is in error prior to providing a signal to said switch controller indicative of said desired beam path.

25. The apparatus of claim 23, wherein said central computer determines that said beam request signal is in error if said beam request signal directs said radiation beam to more than one beam treatment location simultaneously and, if said beam request signal is in error, said central computer does not send said signal to said switch controller indicative of said desired beam path.

26. A method of radiation beam security for a radiation beam therapy system having a radiation beam source, a plurality of radiation beam treatment locations and a plurality of beam treatment paths between said radiation beam source and said plurality of treatment locations wherein said radiation beam therapy system includes a plurality of switches for directing said treatment beam along said plurality of paths, said method comprising:

receiving a beam request signal from a selected treatment location;

inducing a selected set of said plurality of switches to enter a first state in response to said beam request signal whereby said treatment beam will be directed along a selected path of said plurality of paths to said selected beam treatment location;

verifying that said selected set of said plurality of switches are in said first state;

verifying that said switches not in said selected set do not direct said beam along one of said plurality of paths;

allowing beam transport along said selected beam path in response to said verifying steps;

sensing said state of said switches not in said selected set; and interrupting beam transport upon sensing said switches not in said selected set may direct said radiation beam along a non-selected path.

27. The method of claim 26, wherein said step of sensing said state of said switches not in said selected set comprises sensing whether said switches not in said selected steps are in said first state and wherein said interrupting set comprises interrupting transport of said beam upon sensing that one or more of said switches that are not in said selected state are in said first state.

28. The method of claim 27, further comprising the step of:

sensing said state of said switches in said selected set during beam transport; and interrupting beam transport upon sensing that one or more of said switches in said selected set do not permit transport of said beam to said selected treatment location.

\* \* \* \* \*